(12) United States Patent
Ogino et al.

(10) Patent No.: US 10,364,460 B2
(45) Date of Patent: Jul. 30, 2019

(54) REACTION CONTAINER, NUCLEIC ACID ANALYSIS DEVICE, AND NUCLEIC ACID ANALYSIS METHOD

(71) Applicant: TOPPAN PRINTING CO., LTD., Tokyo (JP)

(72) Inventors: Masayuki Ogino, Tokyo (JP); Tomohiko Azuma, Tokyo (JP); Kenichi Sakane, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 425 days.

(21) Appl. No.: 15/082,759

(22) Filed: Mar. 28, 2016

(65) Prior Publication Data

US 2016/0208315 A1 Jul. 21, 2016

Related U.S. Application Data

(63) Continuation of application No. PCT/JP2014/075650, filed on Sep. 26, 2014.

(30) Foreign Application Priority Data

Sep. 30, 2013 (JP) ................................. 2013-205852

(51) Int. Cl.
   *C12Q 1/68* (2018.01)
   *C12Q 1/686* (2018.01)
   (Continued)

(52) U.S. Cl.
   CPC ............... *C12Q 1/686* (2013.01); *C12Q 1/68* (2013.01); *G01N 21/6428* (2013.01);
   (Continued)

(58) Field of Classification Search
   None
   See application file for complete search history.

(56) References Cited

U.S. PATENT DOCUMENTS

2002/0042125 A1* 4/2002 Petersen ........... B01L 3/502715
                                                    435/287.2
2009/0163524 A1* 6/2009 Johnson ............... C07D 487/04
                                                    514/265.1
(Continued)

FOREIGN PATENT DOCUMENTS

CN          103249488 A      8/2013
EP          1342794 A1       9/2003
(Continued)

OTHER PUBLICATIONS

Extended European Search Report dated May 9, 2017 in corresponding European Patent Application No. 14848790.3.
(Continued)

*Primary Examiner* — Samuel C Woolwine

(57) ABSTRACT

A reaction container includes a base material, an analysis well in which a nucleic acid analysis reagent used for a nucleic acid analysis is positioned, the analysis well being arranged on the base material and configured to analyze a sample containing a nucleic acid, and a quantification well in which a quantification reagent configured to specifically detect the nucleic acid is positioned, the quantification well being arranged on the base material and configured to quantify an amount of the nucleic acid contained in the sample, in which the nucleic acid contained in the sample is distributed into the quantification well and the analysis well.

28 Claims, 10 Drawing Sheets

(51) Int. Cl.
*G01N 21/64* (2006.01)
*G01N 21/25* (2006.01)
*G01N 21/33* (2006.01)

(52) U.S. Cl.
CPC ....... *G01N 21/6486* (2013.01); *G01N 21/253* (2013.01); *G01N 21/33* (2013.01)

(56) References Cited

U.S. PATENT DOCUMENTS

| | | | |
|---|---|---|---|
| 2010/0213063 A1* | 8/2010 | Zenhausern | G01N 21/645 204/452 |
| 2011/0008785 A1* | 1/2011 | Tan | B01L 7/52 435/6.12 |
| 2011/0014605 A1* | 1/2011 | Stone | C12N 15/1003 435/6.19 |
| 2011/0201099 A1* | 8/2011 | Anderson | G01N 21/05 435/287.2 |
| 2011/0203688 A1 | 8/2011 | Reed et al. | |
| 2012/0230887 A1* | 9/2012 | Zucchelli | B01F 11/0002 422/502 |
| 2012/0231456 A1 | 9/2012 | Breidenthal et al. | |
| 2013/0203634 A1* | 8/2013 | Jovanovich | B01L 3/502738 506/26 |
| 2013/0216779 A1* | 8/2013 | Hofmeister | G03F 7/0002 428/141 |
| 2014/0335526 A1* | 11/2014 | Garvin | C12Q 1/6888 435/6.12 |
| 2016/0122801 A1* | 5/2016 | Tajima | B01J 19/0046 435/6.12 |

FOREIGN PATENT DOCUMENTS

| | | |
|---|---|---|
| JP | 2004-93297 | 3/2004 |
| JP | 2004-212050 | 7/2004 |
| JP | 2006-346626 | 12/2006 |
| JP | 2008-233002 | 10/2008 |
| JP | 2012-80870 | 4/2012 |
| JP | 4911264 | 4/2012 |
| JP | 4962658 | 6/2012 |
| JP | 2012-185000 | 9/2012 |
| JP | 2012-235749 | 12/2012 |
| JP | 2013-68602 | 4/2013 |
| WO | WO 2010/036808 A1 | 4/2010 |

OTHER PUBLICATIONS

Farrell et al.: "RNA isolation and identification of experimental guidelines—RNA research methods," RNA Methodologies: A Laboratory Guide for Isolation and Characterization, Chemical Industry Press, 3$^{rd}$ edition Jan. 1, 2008.

Chinese Office Action dated Jul. 24, 2017 in corresponding Chinese Patent Application No. 201480053643.0.

Singaporean Office Action dated Nov. 21, 2016 in corresponding Singaporean Patent Application No. 11201602389U.

Chinese Office Action dated Nov. 21, 2016 in corresponding Chinese Patent Application No. 201480053643.0.

International Search Report dated Dec. 16, 2014, in corresponding International Application No. PCT/JP2014/075650.

Raja, S. et al., "Technology for Automated, Rapid, and Quantitative PCR or Reverse Transcription-PCR Clinical Testing", *Clinical Chemistry*, 51:5, 2005, pp. 882-890.

European Office Action dated Nov. 27, 2018, in corresponding European Patent Application No. 14 848 790.3, 6 pgs.

European Office Action dated May 17, 2018, in corresponding European Patent Application No. 14 848 790.3, 6 pgs.

* cited by examiner

REACTION CONTAINER, NUCLEIC ACID ANALYSIS DEVICE, AND NUCLEIC ACID ANALYSIS METHOD

CROSS REFERENCE TO RELATED APPLICATIONS

This application is a continuation application based on a PCT Patent Application No. PCT/JP2014/075650, filed Sep. 26, 2014, whose priority is claimed on Japanese Patent Application No. 2013-205852, filed Sep. 30, 2013, the entire content of which are hereby incorporated by reference.

BACKGROUND OF THE INVENTION

Field of the Invention

The present invention relates to a reaction container, a nucleic acid analysis device including the reaction container, and a nucleic acid analysis method.

Description of the Related Art

"Order-made (personalized) medicine" that provides an effective treatment and an effective medication method depending on a genetic background which a patient has on the basis of epidemiological and scientific grounds is expected not only to improve QOL (quality of life) of each individual, but also to suppress an increase of medical expenses along with side effects of drugs. Various techniques are present in determining the effects or the side effects of the drugs, but a gene diagnosis that analyzes differences of genes between individuals is one of the effective techniques. It is preferable that the order-made (personalized) medicine be capable of making a simple and quick diagnosis in the field. As a technique for realizing a simple and quick diagnosis, a technology which is referred to as μ-TAS (Total Analysis System) being a reaction device which deals with a very small amount of a sample solution containing the gene, or Lab-on-Chip is used.

This is a device including a plurality of reaction chambers and flow paths in one chip or one cartridge, and can deal with analyses of a plurality of analytes, or a plurality of types of items at the same time. These technologies are techniques having various advantages such that it is possible to make the handled drugs into a small amount by miniaturizing the chip and the cartridge. An outline of a gene analysis has processes of taking out nucleic acid by extracting or purifying the nucleic acid for the gene analysis from a biological sample such as blood, oral mucosa or sputum which is collected from the patient, amplifying a gene region to be examined and a nucleic acid sequence to be examined by PCR or the like, and detecting a specific sequence in a check target such as a genotype.

In Japanese Unexamined Patent Application, First Publication No. 2004-212050, Japanese Unexamined Patent Application, First Publication No. 2004-093297, and Clinical Chemistry 51: 882-890, 2005, a gene diagnosis device in which processes such as amplification and detection proceed in a fully automatic manner after nucleic acid is taken out from a biological sample is disclosed.

When the process of extracting the nucleic acid is independent from the subsequent processes of amplifying and detecting, it is possible to confirm the amount of the nucleic acid by an operation using an external device. However, in the device which is disclosed in Japanese Unexamined Patent Application, First Publication No. 2004-212050, Japanese Unexamined Patent Application, First Publication No. 2004-093297, and Clinical Chemistry 51: 882-890, 2005, the processes of amplifying and detecting proceed in a fully automatic manner after the nucleic acid is extracted from the biological sample, and it is not possible to confirm the amount of the obtained nucleic acid. Therefore, the amount of the nucleic acid taken out is unclear, and it is not sufficient in a case where the check target is aimed at detecting gene mutation or the like.

For example, in the case of gene mutation which is represented by cancer or the like, when 99.9% in total is normal wild type, and it is desired to detect a variant of the remainder of 0.1%, it is not possible to secure that the mutation is 0.1% unless the amount of the nucleic acid necessary before the amplifying is 1000 copies or more.

Moreover, it is considered that when an irregular result is output in the analysis of the presence and absence of a particular nucleic acid sequence or gene polymorphism, it is not possible to differentiate whether the amount of the nucleic acid is insufficient or a phenomenon is caused by mixing a reaction inhibition material or the like into a system.

In this manner, there is a case where the amount of the nucleic acid is unclear in a fully automatic gene analysis system, and reliability of the analysis result depends on properties of the check items.

The present invention is made in consideration of the above circumstances, and an object thereof is to provide a reaction container that is suitably used in a fully automatic gene analysis system and capable of quantifying nucleic acid obtained by extraction from a biological sample, and capable of analyzing the nucleic acid, a nucleic acid analysis device including the reaction container, and a nucleic acid analysis method.

SUMMARY

A reaction container according to a first aspect of the present invention, includes a base material; an analysis well in which a nucleic acid analysis reagent used for a nucleic acid analysis is positioned, the analysis well being arranged on the base material and configured to analyze a sample containing a nucleic acid; and a quantification well in which a quantification reagent configured to specifically detect the nucleic acid is positioned, the quantification well being arranged on the base material and configured to quantify an amount of the nucleic acid contained in the sample, in which the nucleic acid contained in the sample is distributed to into the quantification well and the analysis well.

In the first aspect, the base material may be formed from a resin having light-transmitting properties.

The reaction container according to the first aspect may further include a flow path arranged on the base material, and an injection port which is arranged on the base material and configured so that a solution is injected into the injection port, in which by the flow path the nucleic acid contained in the sample may be distributed into the quantification well and the analysis well.

In the first aspect, at least one of the quantification reagent and the nucleic acid analysis reagent may be positioned in a dry state.

In the first aspect, at least one of the quantification reagent and the nucleic acid analysis reagent may be positioned in the dry state, and in a state of being mixed with trehalose.

A nucleic acid analysis device according to a second aspect of the present invention, includes the reaction container according to the first aspect, and an extraction section extracting the nucleic acid.

The nucleic acid analysis device according to the second aspect may further include a purification section purifying the nucleic acid.

A nucleic acid analysis method according to a third aspect of the present invention, is a nucleic acid analysis method using the reaction container according to the first aspect, or the nucleic acid analysis device according to the second aspect, the method including a nucleic acid quantification process of injecting a sample containing the same nucleic acid as the nucleic acid analyzed in the analysis well into the quantification well, forming an association state in which the nucleic acid contained in the sample and the quantification reagent are associated in the quantification well, measuring a signal which is emitted in the association state, and calculating an amount of the nucleic acid analyzed in the analysis well from the measured signal.

The nucleic acid analysis method according to the third aspect may further include a nucleic acid extraction process of extracting nucleic acid from a biological sample performed before the nucleic acid quantification process, and a nucleic acid analysis process of performing identification of the nucleic acid in the analysis well by injecting the sample containing the nucleic acid into the analysis well performed after the nucleic acid extraction process, in which the nucleic acid may be obtained in the nucleic acid extraction process.

The nucleic acid analysis method according to the third aspect may further include a process of determining validity of an analysis result obtained by the nucleic acid analysis process based on the amount of the nucleic acid calculated by the nucleic acid quantification process performed after the nucleic acid quantification process.

The nucleic acid analysis method according to the third aspect may further include a nucleic acid purification process performed after the nucleic acid extraction process and before the nucleic acid quantification process.

In the third aspect, the nucleic acid analysis process may be performed after the nucleic acid quantification process, and a nucleic acid purification process performed after the nucleic acid quantification process and before the nucleic acid analysis process may be included.

In the third aspect, the nucleic acid analysis process may be performed after the nucleic acid quantification process, and a process of determining whether or not a transition to the nucleic acid analysis process is performed according to the amount of the nucleic acid calculated by the nucleic acid quantification process, which is performed after the nucleic acid quantification process and before the nucleic acid analysis process may be further included.

The nucleic acid analysis method according to the third aspect may further include a process of determining whether or not a transition to the nucleic acid purification process is performed according to the amount of the nucleic acid calculated by the nucleic acid quantification process, which is performed after the nucleic acid quantification process and before the nucleic acid purification process.

In the third aspect, the biological sample may be at least one selected from the group of whole blood, serum, saliva, sputum, oral mucosa, and a tissue slice.

A reaction container according to a fourth aspect of the present invention, includes an analysis well in which a nucleic acid analysis reagent used for a nucleic acid analysis is positioned, the analysis well being arranged on the base material and configured to analyze a sample containing a nucleic acid; and a quantification well arranged on the base material and configured to quantify an amount of the nucleic acid contained in the sample, in which the nucleic acid contained in the sample is distributed into the quantification well and the analysis well.

In the fourth aspect, the base material may be formed from a resin having light-transmitting properties.

The reaction container according to the fourth aspect may further include a flow path arranged on the base material, and an injection port arranged on the base material and configured so that a solution is injected into the injection port, in which by the flow path the nucleic acid contained in the sample may be distributed into the quantification well and the analysis well.

According to a fifth aspect of the present invention, a nucleic acid analysis device is provided, including the reaction container according to the fourth aspect, and an extraction section extracting the nucleic acid.

The nucleic acid analysis device according to the fifth aspect may further include a purification section purifying the nucleic acid.

A nucleic acid analysis according to a sixth aspect of the present invention, is a nucleic acid analysis method using the reaction container according to the fourth aspect, or the nucleic acid analysis device according to the fifth aspect, the method including a nucleic acid quantification process of injecting a sample containing the same nucleic acid as the nucleic acid analyzed in the analysis well into the quantification well, measuring ultraviolet absorbance of the sample in the quantification well, and calculating an amount of the nucleic acid analyzed in the analysis well from the measured ultraviolet absorbance.

The nucleic acid analysis method according to the sixth aspect may further include a nucleic acid extraction process of extracting nucleic acid from a biological sample performed before the nucleic acid quantification process, and a nucleic acid analysis process of performing identification of the nucleic acid in the analysis well by injecting the sample containing the nucleic acid into the analysis well performed after the nucleic acid extraction process in which the nucleic acid may be obtained in the nucleic acid extraction process.

The nucleic acid analysis method according to the sixth aspect may further include a process of determining validity of an analysis result obtained by the nucleic acid analysis process based on the amount of the nucleic acid calculated by the nucleic acid quantification process performed after the nucleic acid quantification process.

The nucleic acid analysis method according to the sixth aspect may further include a nucleic acid purification process performed after the nucleic acid extraction process and before the nucleic acid quantification process.

In the sixth aspect, the nucleic acid analysis process may be performed after the nucleic acid quantification process, and a nucleic acid purification process performed after the nucleic acid quantification process and before the nucleic acid analysis process may be included.

In the sixth aspect, the nucleic acid analysis process may be performed after the nucleic acid quantification process, and a process of determining whether or not a transition to the nucleic acid analysis process is performed according to the amount of the nucleic acid calculated by the nucleic acid quantification process, which is performed after the nucleic acid quantification process and before the nucleic acid analysis process, may be further included.

The nucleic acid analysis method according to the sixth aspect may further include a process of determining whether or not a transition to the nucleic acid purification process is performed according to the amount of the nucleic acid calculated by the nucleic acid quantification process, which is performed after the nucleic acid quantification process and before the nucleic acid purification process.

In the sixth aspect, the biological sample may be at least one selected from the group of whole blood, serum, saliva, sputum, oral mucosa, and a tissue slice.

According to the aspects of the present invention, it is possible to confirm the amount of the nucleic acid obtained by the nucleic acid extraction from the biological sample, and it is possible to improve reliability with respect to the analysis result of the nucleic acid.

DETAILED DESCRIPTION OF THE PREFERRED EMBODIMENTS

<<Reaction Container>>
[First Embodiment]

A reaction container according to a first aspect of the present invention includes an analysis well in which a nucleic acid analysis reagent used for a nucleic acid analysis is positioned on a base material, the analysis well configured to analyze a sample containing nucleic acid, and a quantification well in which a quantification reagent configured to specifically detect a nucleic acid, and the quantification well configured to quantify an amount of the nucleic acid contained in the sample. In the reaction container according to a first aspect of the present invention, the nucleic acid contained in the sample may be distributed into the quantification well and the analysis well.

Moreover, the reaction container according to the first aspect of the present invention is preferably a reaction container that further includes a flow path, and an injection port arranged on the base material and configured so that a solution is injected into the injection port, and by the flow path, the nucleic acid contained in the sample may be distributed into the quantification well and the analysis well.

Figure 1:
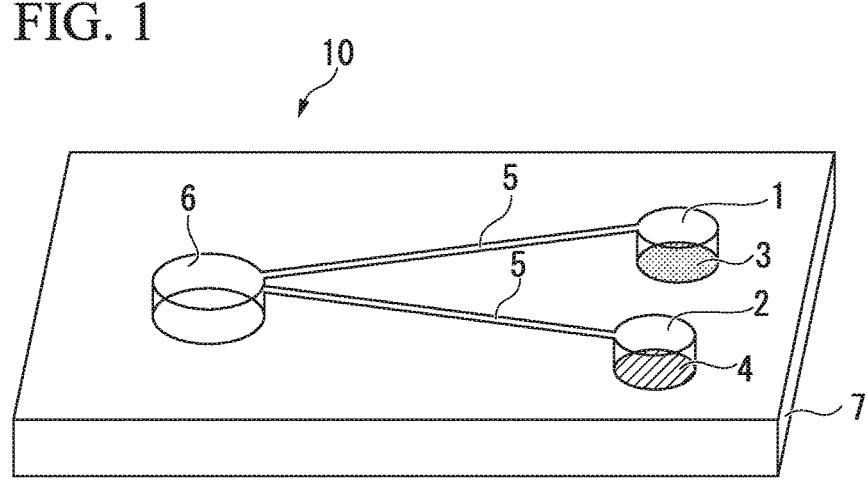
FIG. 1 is a perspective diagram illustrating a reaction container according to a first embodiment of the present invention.

The reaction container according to the first embodiment of the present invention will be described with reference to FIG. 1. As illustrated in FIG. 1, a reaction container 10 according to the first embodiment of the present invention includes a base material 7 including an analysis well 1 that is capable of analyzing the sample containing the nucleic acid by positioning a nucleic acid analysis reagent 3 used for the nucleic acid analysis, a quantification well 2 that is capable of quantifying the amount of the nucleic acid contained in the sample by positioning a quantification reagent 4 which is capable of specifically detecting the nucleic acid, a flow path 5, and an injection port 6 into which the solution can be injected. By the flow path 5, the sample which is injected into the flow path 5 from the injection port 6 may be distributed into the quantification well 2 and the analysis well 1.

In the present invention, the "nucleic acid" refers to DNA, RNA or an analogue thereof, and may be a natural nucleic acid, or may be a synthesized nucleic acid. As the analogue, artificial nucleic acid such as PNA or LNA is used. As the natural nucleic acid, for example, there is genome DNA, mRNA, tRNA, rRNA, or hnRNA which are collected from a living organism. Moreover, as the synthesized nucleic acid, there are DNA which is synthesized by a known chemical synthesis method such as a β-cyanoethyl phosphoramidite method, or a DNA solid phase synthesis method, nucleic acid synthesized by a known nucleic acid amplification method such as PCR, cDNA which is synthesized by a reverse transcription reaction, or the like.

Figure 2:
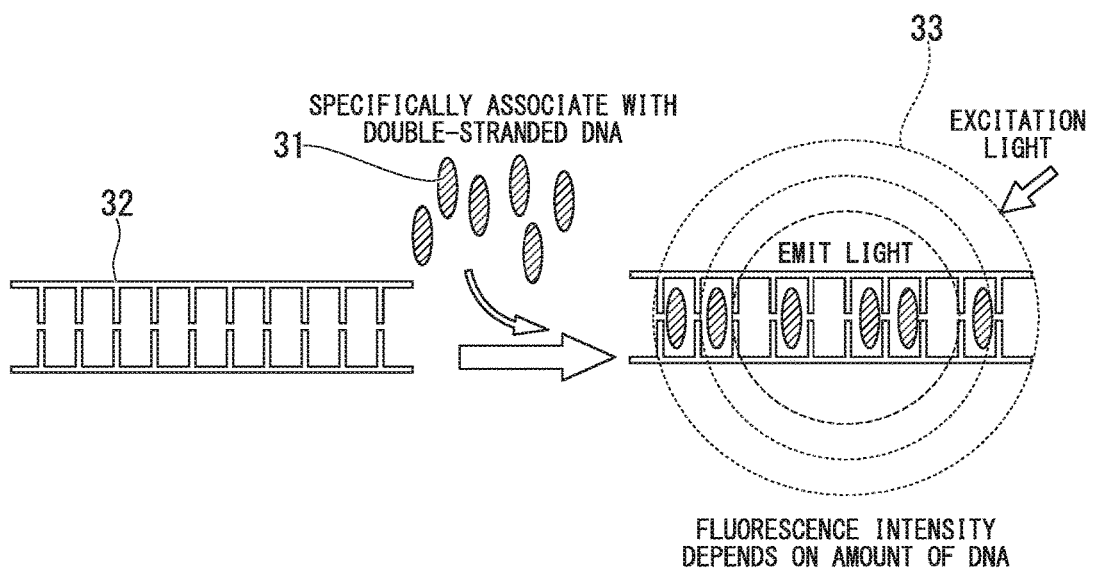
FIG. 2 is a schematic diagram illustrating a measurement principle of an amount of a nucleic acid using a fluorescent material.

The "quantification reagent which is capable of specifically detecting the nucleic acid" is a material that emits a signal indicating an association state by being associated with the nucleic acid, and is not particularly limited as long as it is a reagent which is capable of quantifying the amount of the nucleic acid by a change of the signal depending on the amount of the nucleic acid in the sample solution. The "quantification reagent which is capable of specifically detecting the nucleic acid" is preferably a material that emits fluorescence by being specifically associated with the nucleic acid, and is further preferably a material that emits fluorescence after being specifically associated with double-stranded DNA. As the material, for example, SYBRGreen, PicoGreen, EvaGreen, ethidium bromide, Hoechst 33258 (CAS number 23491-45-4; phenol-(4-[5-(4-methyl-1-piperazinyl)[2,5'-bi-1H-benzoimidazole]-2'-yl])-trihydrochloric acid), TOTO-1, YOYO-1, YO-PRO-1, BEBO, BETO, BOXTO or the like, is used. FIG. 2 is a schematic diagram illustrating a reaction mechanism in which a fluorochrome 31 emits a signal 33 by specifically bonding to double-stranded DNA 32, and being irradiated with excitation light. In this case, the change of the signal is the change of fluorescence intensity.

"Analyzing the sample containing the nucleic acid" means identifying the nucleic acid information such as a base sequence of the nucleic acid contained in the sample or nucleic acid modification, and also includes identifying information indirectly indicating the information, in addition to the information indicating the base sequence of the nucleic acid or the nucleic acid modification. As the information indirectly indicating the information, for example, it is possible to exemplify detection of the presence or absence of double-stranded nucleic acid formation which is generated from a difference of the base sequence. As the identified information of the base sequence of the nucleic acid, it is preferable that a gene sequence be made up of sequences which include the base sequence of the nucleic acid of the identification target, and it is more preferable that gene mutation of the gene be identified. The gene mutation is preferably a difference of the base sequence of the gene which is present between individuals of the same biological species. In detail, by substituting, deleting, or inserting one base or a plurality of bases in the base sequence, the difference of the base sequence is generated. As such a gene mutation, for example, SNP or CNV (Copy Number variation) polymorphism, base deletion mutation, base insertion mutation, translocation mutation or the like, is exemplified. Moreover, the gene mutation of the present invention also includes acquired mutation such as somatic cell mutation which is the difference of the base sequence of the gene which is present between cells in the same individual, in addition to inborn mutation such as the gene polymorphism of SNP. Furthermore, in the analysis, it is preferable that the amplification of the nucleic acid of an analysis target be performed.

The "nucleic acid analysis reagent" is not particularly limited as long as it is a reagent which is used in the identification of the nucleic acid information, and is preferably a reagent which is used in the amplification of the nucleic acid at the time of the identification. As an ingredient which is contained in the reagent, oligo primer set, nucleic acid synthesis enzyme, nucleoside or the like, is used, and various combinations which are necessary for general nucleic acid amplification may be used.

Moreover, in the nucleic acid analysis reagent, a material that is capable of detecting the presence or absence of the double-stranded nucleic acid formation may be included, in addition to a molecule which is used in the amplification of the nucleic acid. In the material, a material which is capable of specifically detecting the nucleic acid described above is also included.

As "Positioning the reagent", the reagent may be positioned in the analysis well or the quantification well before the nucleic acid contained in the sample is distributed into the quantification well or the analysis well. Moreover, the reagent may be positioned in the analysis well or the quantification well after the nucleic acid contained in the sample is distributed into the quantification well or the analysis well. It is preferable that the reagent be positioned in the analysis well or the quantification well in advance before the nucleic acid contained in the sample is distributed into the quantification well and the analysis well.

As a method for positioning the reagent after the nucleic acid contained in the sample is distributed into the quantification well or the analysis well, for example, a method for separately arranging the respective reagent wells which accommodate the reagent from the quantification well or the analysis well, communicating the respective reagent wells with the quantification well or the analysis well after the nucleic acid is distributed into the wells, and thereby positioning the reagent, is used.

As a method for positioning the reagent before the nucleic acid contained in the sample is distributed into the quantification well or the analysis well, a method for drying and fixing the reagent onto an inner wall of the quantification well or the analysis well is used.

Accordingly, in the embodiment, it is preferable that at least one of the quantification reagent and the nucleic acid analysis reagent be positioned in a dry state, and it is more preferable that at least one of the quantification reagent and the nucleic acid analysis reagent be positioned in the dry state, and in a state of being mixed with trehalose. By positioning the reagent in the dry state, it is possible to reduce deterioration of the reagent. Furthermore, by positioning the reagent in the state of being mixed with trehalose, it is possible to further reduce the deterioration of the reagent.

As a method for fixing the reagent, for example, dropping the liquid reagent with a pipette in a well section of a first base material 7, and centrifuging the base material in a centrifugal device at 2000 rpm to 3000 rpm for approximately 5 minutes so that a liquid surface of an appropriate amount of a liquid reagent remains in a flat state and it is possible to fix the reagent to the well by drying the remaining liquid reagent.

Moreover, all of the materials which are contained in the reagent may not be positioned before the nucleic acid is distributed into the quantification well or the analysis well. The reagent may be separately positioned before and after the nucleic acid is distributed into the quantification well or the analysis well. As such an example, for example, a case where the sample is injected into the analysis well to which the material that is used in the amplification of the nucleic acid among the nucleic acid analysis reagent is fixed in advance, and the material that is capable of detecting the amount of the amplified nucleic acid after the nucleic acid is amplified is injected into the analysis well, is used.

Figure 3A:
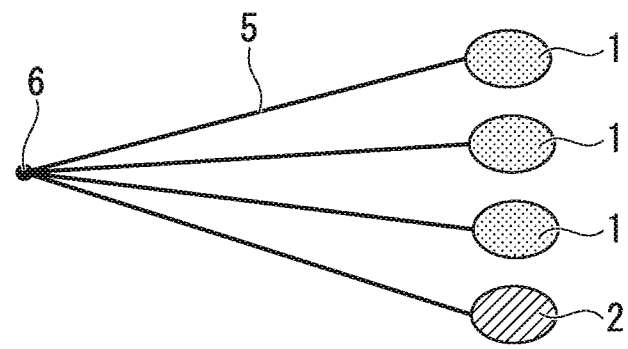
FIG. 3A is a schematic diagram illustrating a flow path in the reaction container according to the first embodiment or a second embodiment of the present invention.
Figure 3B:
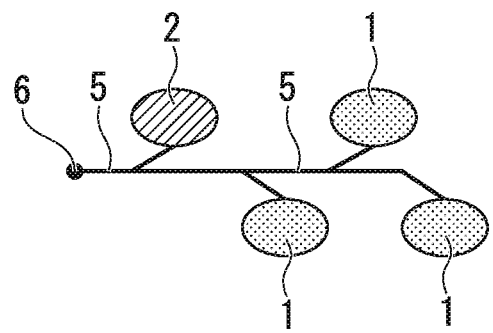
FIG. 3B is a schematic diagram illustrating the flow path in the reaction container according to the first embodiment or the second embodiment of the present invention.
Figure 3C:
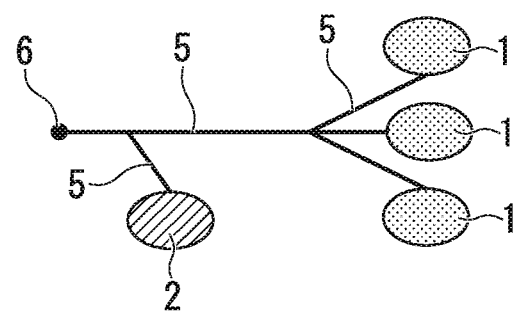
FIG. 3C is a schematic diagram illustrating the flow path in the reaction container according to the first embodiment or the second embodiment of the present invention.

The reaction container of the embodiment includes a flow path that is capable of distributing the nucleic acid contained in the sample into the quantification well and the analysis well. Although positions of branches or directions of the flow path are not particularly limited, for example, it is possible to exemplify configurations as illustrated in FIG. 3A to FIG. 3C. From the viewpoint of being capable of quantifying the amount of the nucleic acid obtained by the nucleic acid extraction from a biological sample before the analysis of the sample containing the nucleic acid, it is preferable that the quantification well 2 be positioned to be closer to the injection port 6 than the analysis well 1. Thereby it is possible to facilitate that the nucleic acid is distributed into the quantification well earlier than the analysis well.

Moreover, for example, if using the configuration illustrated in FIG. 3B or FIG. 3C, by arranging a damming section of the sample solution which is capable of opening and closing of the flow path at the position of the flow path which is closer to the analysis well than a branch point of the flow path connecting to the quantification well and the flow path connecting to the analysis well, it is possible to determine whether or not liquid feeding to the analysis well is performed by the amount of the nucleic acid calculated in the quantification well, and it is possible to control the liquid feeding.

The base material 7 of the reaction container of the embodiment is preferably a resin having light-transmitting properties. As a material of the base material 7, it is possible to suitably use a resin having light-transmitting properties. Moreover, when an optical analysis (such as fluorescence measurement or colorimetric measurement) is made with respect to the solution of the analysis well 1 or the quantification well 2, it is preferable that transparency of the base material 7 be high. For example, the material of the base material 7 is not particularly limited as long as it is a material which has no influence on the sample, but if a resin material including any of polypropylene, polycarbonate, and acryl is particularly used, it is possible to secure good visible light-transmitting properties. As the polypropylene, it is possible to use a random copolymer of polyethylene with homopolypropylene or polypropylene. Moreover, as the acryl, it is possible to use a copolymer of a monomer such as methacrylic acid esters, other methacrylic acid esters, acrylic acid ester, styrene, and polymethyl methacrylate. Still further, when the resin material is used, it is possible to secure heat resistance and strength of the reaction container. In addition to the resin materials, it is possible to use metallic materials such as aluminum, copper, silver, nickel, brass, and gold. When the metallic material is used, it is additionally excellent in heat conductivity and sealing performance.

Furthermore, by making a bottom section of the analysis well 1 or the quantification well 2 of the base material 7 be transparent, it is possible to perform the detection or the analysis of the fluorescence from the outside. In "transparent" and "light-transmitting properties" of the embodiment, it is preferable that total average transmittance of a light range (wavelength of 230 nm to 780 nm) at the time of forming the base material 7 be 70% or more.

As a processing method of the base material 7, in the case of the resin material, it is possible to use various types of resin-forming methods such as injection molding and vacuum molding, machine cutting or the like. In the case of the metallic material, it is possible to form the base material 7 by performing grinding or etching by using a thick base material, or performing pressing or drawing in a thin metal sheet.

Moreover, it is preferable that a thickness of the base material 7 be in the range of 50 µm to 3 mm, in order to secure good light-transmitting properties, good heat resistance, and good strength, and in order to reliably perform the processing of a concave section.

[Second Embodiment]

A reaction container according to a second embodiment of the present invention include an analysis well in which a nucleic acid analysis reagent used for a nucleic acid analysis is positioned, the analysis well being configured to analyze the sample containing the nucleic acid, and a quantification well configured to quantify the amount of the nucleic acid contained in the sample, and is configured so that the nucleic acid contained in the sample is distributed into the quantification well and the analysis well. The details thereof will be omitted since they are described in the first embodiment, but in the quantification well of the reaction container of the embodiment, the quantification reagent may not be positioned, and it is suitably used in a case where the amount of the nucleic acid is quantified without using the reagent. For example, a case where the amount of the nucleic acid in the sample is calculated by the irradiation of ultraviolet light is exemplified.

As described in the above embodiment, both of the analysis well 1 and the quantification well 2 are arranged on the same base material, and the amount of the nucleic acid contained in the sample is measured under the same environments. Therefore, it is possible to obtain the amount of the nucleic acid contained in the sample before the analysis of the nucleic acid is performed in the analysis well with high reliability in the quantification well.

<<Nucleic Acid Analysis Device>>

[Third Embodiment]

Figure 4:
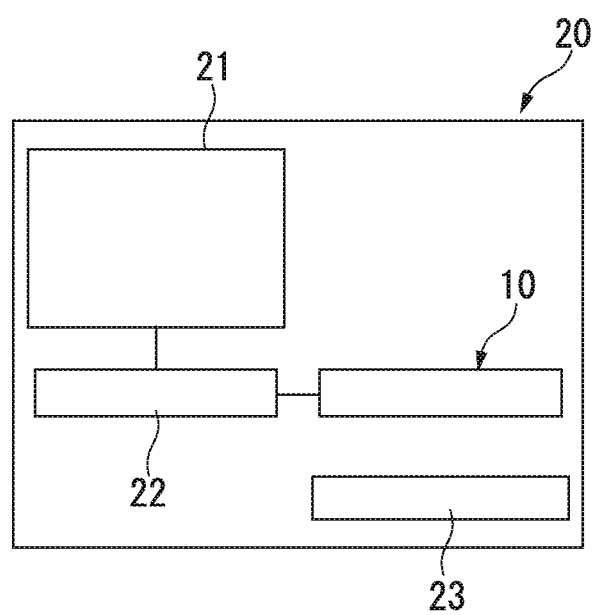
FIG. 4 is a diagram illustrating an example of a configuration of a nucleic acid analysis device according to a third embodiment of the present invention.

A nucleic acid analysis device according to a third embodiment of the present invention includes the reaction container described above, an extraction section that extracts the nucleic acid, and a purification section that purifies the nucleic acid obtained in the extraction section. Moreover, it is preferable that the nucleic acid analysis device of the embodiment include a measurement section which optically analyzes the solution in the analysis well 1 or the quantification well 2. The extraction section and the purification section may be arranged on the base material as a part of the reaction container of the present invention, but may be configured separately from the reaction container. A schematic diagram of a configuration of the nucleic acid analysis device according to the embodiment is illustrated in FIG. 4. A nucleic acid analysis device 20 includes the reaction container 10, an extraction section 21, a purification section 22, and a measurement section 23. The solution of each sample containing the nucleic acid obtained by the extraction section 21, the purification section 22, and the reaction container 10 is fed to the other sections of the nucleic acid analysis device 20 or the reaction container, and thereby the nucleic acid analysis is performed. In the extraction section 21, the reagent to perform the nucleic acid extraction from the sample is included. Such reagents are known, and suitable reagents may be appropriately selected depending on the type of sample from which the nucleic acid is derived. Moreover, it is preferable that a carrier having property to adsorb the nucleic acid be included in the purification section 22. As such a material of the carrier, it is possible to exemplify a fiber material such as silica or glass wool.

In this manner, the nucleic acid analysis device 20 including the reaction container 10 may easily analyze the amount of nucleic acid contained in the sample obtained in the extraction section or the purification section with high reliability, without taking out the sample from the nucleic acid analysis device 20.

<<Nucleic Acid Analysis Method>>

[Fourth Embodiment]

A nucleic acid analysis method according to a fourth embodiment of the present invention is a nucleic acid analysis method using the reaction container described above, or the nucleic acid analysis device described above, and is a nucleic acid analysis method including a nucleic acid quantification process B that includes b1) a process of injecting the sample containing the same nucleic acid as the nucleic acid which may be analyzed in the analysis well into the quantification well, b2) a process of forming an association state in which the nucleic acid contained in the sample and the quantification reagent are associated in the quantification well, b3) a measurement process of measuring a signal which is emitted in the association state, and b4) a process of calculating the amount of the nucleic acid contained in the sample which may be analyzed in the analysis well from the signal which is measured in the measurement process, further including a nucleic acid extraction process A of performing the nucleic acid extraction from the biological sample performed before the nucleic acid quantification process B, and a nucleic acid analysis process C of performing identification of the nucleic acid in the analysis well by injecting the sample containing the nucleic acid into the analysis well performed after the nucleic acid extraction process A, in which the nucleic acid is the nucleic acid obtained in the nucleic acid extraction process A. The "same nucleic acid as the nucleic acid which may be analyzed in the analysis well" means the nucleic acid having the same composition as the nucleic acid which may be analyzed in the analysis well, so as to calculate the amount of the nucleic acid which may be analyzed in the analysis well.

Figure 5:
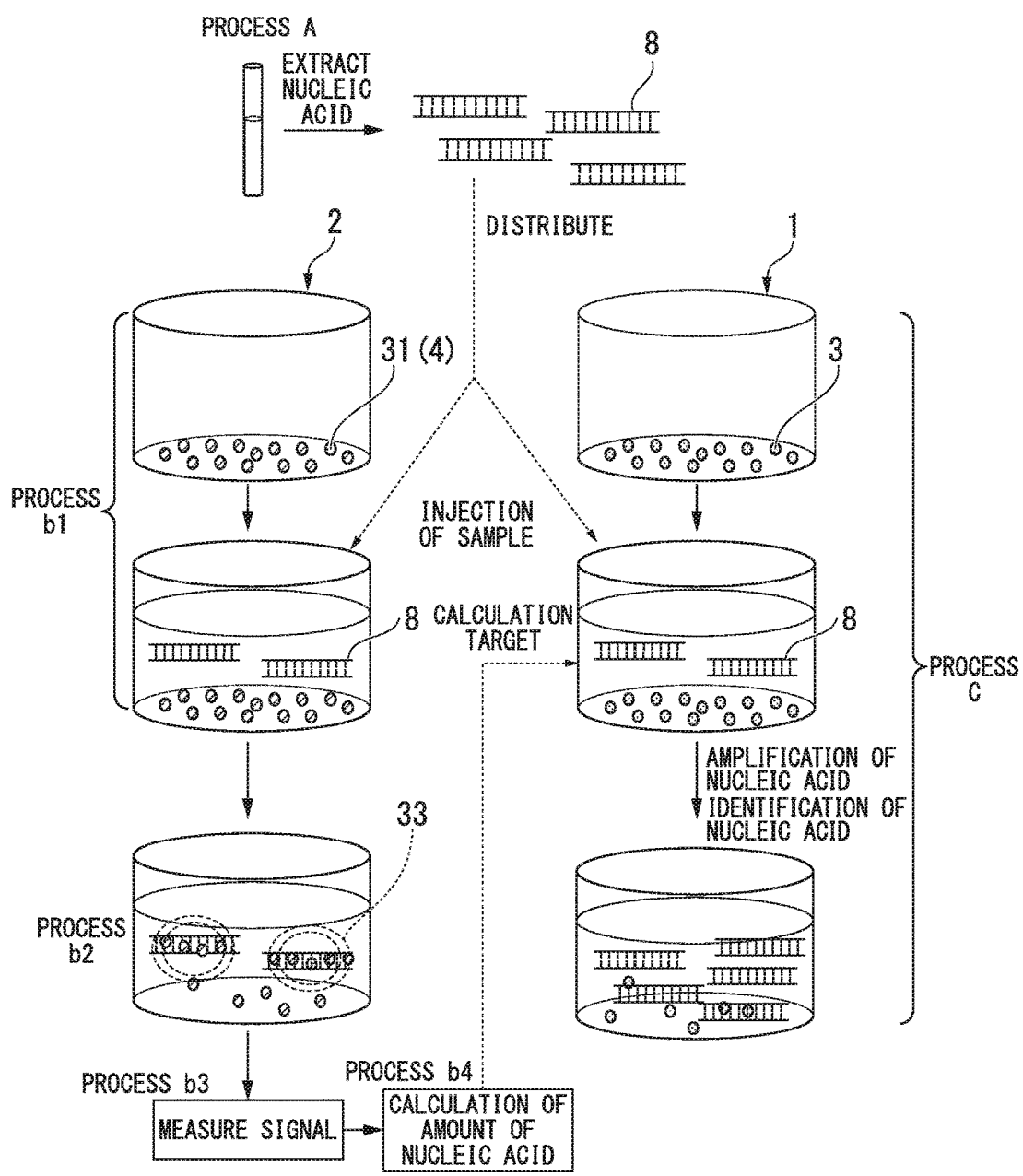
FIG. 5 is a diagram schematically illustrating a nucleic acid analysis method according to a fourth embodiment of the present invention.
Figure 6:
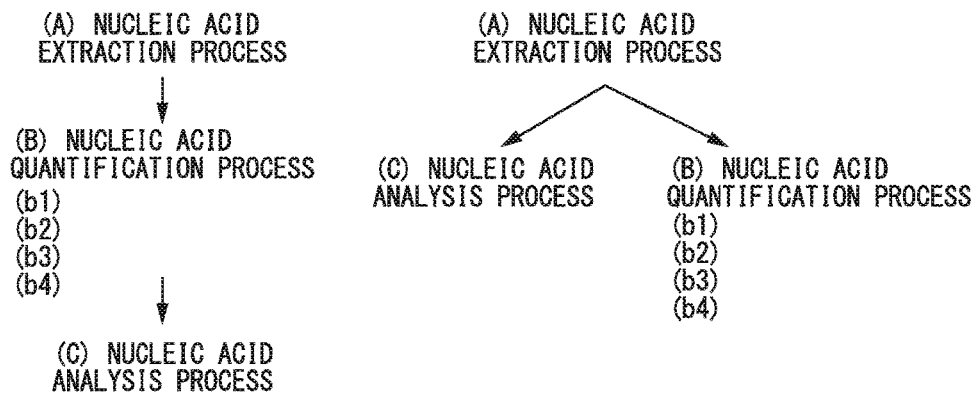
FIG. 6 is a flowchart illustrating the nucleic acid analysis method according to the fourth embodiment of the present invention.

Hereinafter, the nucleic acid analysis method according to the embodiment will be described with reference to FIG. 5. First, the nucleic acid is extracted from the biological sample, and a nucleic acid 8 is obtained (process A). Furthermore, the process B and the process C may be performed at the same time, or either may be performed ahead. For example, as illustrated in the left of FIG. 6, the process C is performed after the process B, or as illustrated in the right of FIG. 6, the process B and the process C may be performed at the same time. The sample containing the nucleic acid 8 obtained in the process A is injected into the analysis well 1, and the identification of the nucleic acid is performed by the nucleic acid analysis reagent 3 (process C). Similarly, the sample containing the nucleic acid 8 obtained in the process A is injected into the quantification well 2 (process b1). The nucleic acid 8 contained in the sample which is injected into the quantification well 2 and the quantification reagent 4 are associated with each other, and the association state is formed (process b2). Next, a signal 33 that is emitted from the quantification reagent 4 which forms the association state with the nucleic acid 8 is measured (process b3).

Based on strength of the measured signal, the amount of the nucleic acid 8 which is contained in the sample before the amplification of the nucleic acid of the process C is performed is calculated (process b4).

The nucleic acid analysis method may calculate the amount of the nucleic acid before the amplification used for the nucleic acid analysis carried out in the analysis well by including the process B. Therefore, it is possible to improve reliability and accuracy of the nucleic acid analysis result carried out in the analysis well. In particular, since the amount of nucleic acid is important in the analysis of gene mutation, it is significant to confirm whether the amount of the nucleic acid is sufficient before the process C.

[Fifth Embodiment]

A nucleic acid analysis method according to a fifth embodiment of the present invention includes a process D performed after the nucleic acid extraction process A and the nucleic acid quantification process B and determining validity of the analysis result obtained by the nucleic acid analysis process C according to the amount of the nucleic acid calculated by the nucleic acid quantification process B.

Figure 7:
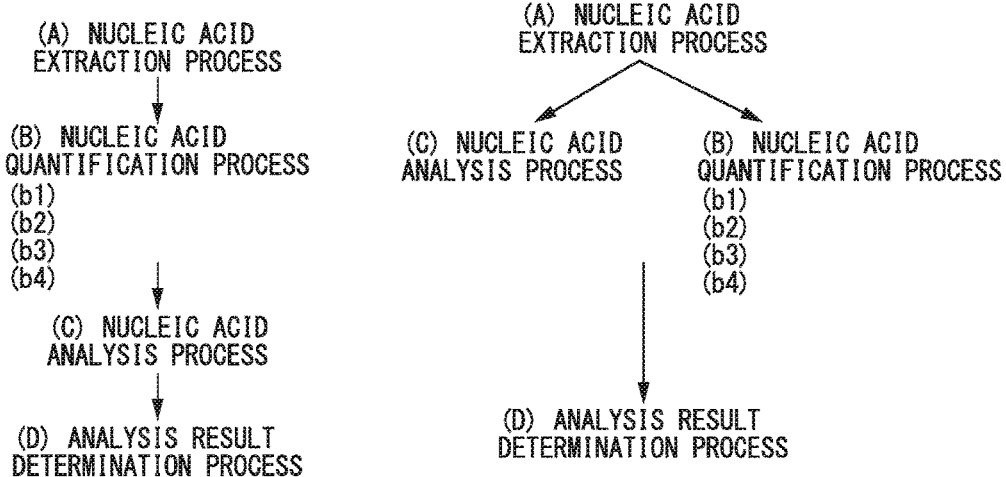
FIG. 7 is a flowchart illustrating a nucleic acid analysis method according to a fifth embodiment of the present invention.

Accrordingly, the process D is performed after the process A, the process B, and the process C. An example of the nucleic acid analysis method according to the embodiment which includes the process D is illustrated in FIG. 7. Since the nucleic acid analysis method includes the process D, the validity of the nucleic acid analysis result is determined, and therefore it is possible to avoid adopting an erroneous analysis result, and realize a quick suggestion of a necessity for a reanalysis or the like.

[Sixth Embodiment]

Figure 8:
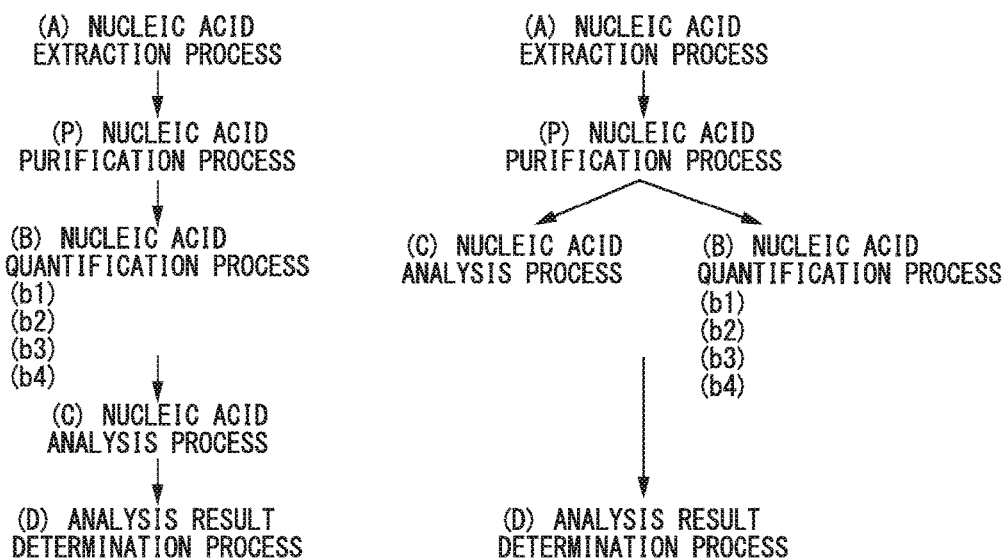
FIG. 8 is a flowchart illustrating a nucleic acid analysis method according to a sixth embodiment of the present invention.

A nucleic acid analysis method according to a sixth embodiment of the present invention further includes a nucleic acid purification process P performed after the nucleic acid extraction process A and before the nucleic acid quantification process B. An example of the nucleic acid analysis method according to the embodiment which includes the process P is illustrated in FIG. 8. The nucleic acid analysis method includes the process P, and thereby purity of the nucleic acid in the sample is improved, and a more accurate nucleic acid analysis becomes possible.

[Seventh Embodiment]

Figure 9:
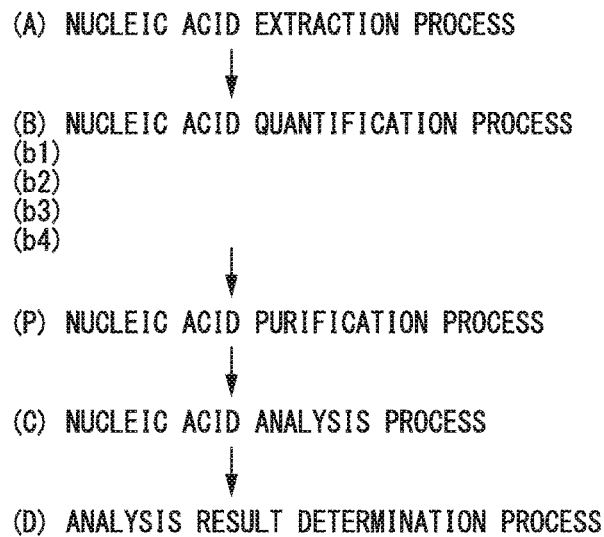
FIG. 9 is a flowchart illustrating a nucleic acid analysis method according to a seventh embodiment of the present invention.

In a nucleic acid analysis method according to a seventh embodiment of the present invention, the nucleic acid analysis process C is performed after the nucleic acid quantification process B, and a nucleic acid purification process P performed after the nucleic acid quantification process B and before the nucleic acid analysis process C is included. An example of the nucleic acid analysis method according to the embodiment which includes the process P is illustrated in FIG. 9. Since the process P is performed after the nucleic acid quantification process B and before the nucleic acid analysis process C, the nucleic acid purification is performed with respect to only the sample analyzed in the process C, and therefore it is possible to reduce the amount of reagent required for the nucleic acid purification.

[Eighth Embodiment]

Figure 10:
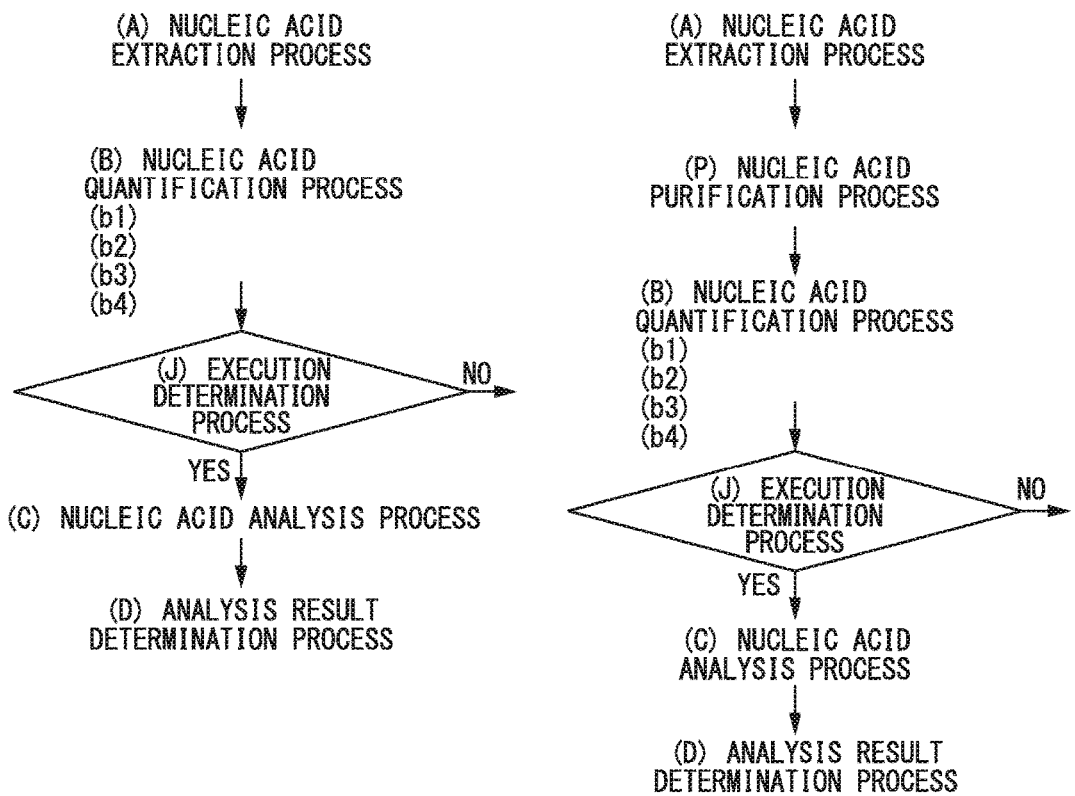
FIG. 10 is a flowchart illustrating a nucleic acid analysis method according to an eighth embodiment of the present invention.

In a nucleic acid analysis method according to an eighth embodiment of the present invention, the nucleic acid analysis process C is performed after the nucleic acid quantification process B, and a process J of determining whether or not a transition to the nucleic acid analysis process C is performed, according to the amount of the nucleic acid calculated by the nucleic acid quantification process B performed after the nucleic acid quantification process B and before the nucleic acid analysis process C is further included. An example of the nucleic acid analysis method according to the embodiment which includes the process J is illustrated in FIG. 10. Since the process J is performed after the nucleic acid quantification process B and before the nucleic acid analysis process C, it is possible to select an interruption of the nucleic acid analysis before the process C is performed, and it is possible to prevent an incorrect nucleic acid analysis result being obtained. Moreover, it is possible to reduce the amount of reagent required for the process C.

[Ninth Embodiment]

Figure 11:
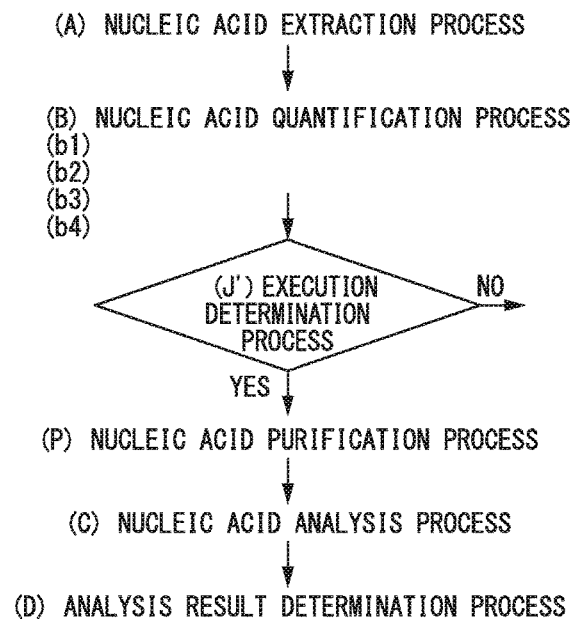
FIG. 11 is a flowchart illustrating a nucleic acid analysis method according to a ninth embodiment of the present invention.

A nucleic acid analysis method according to a ninth embodiment of the present invention further includes a process J' of determining whether or not a transition to the nucleic acid purification process P is performed, according to the amount of the nucleic acid calculated by the nucleic acid quantification process B performed after the nucleic acid quantification process B and before the nucleic acid purification process P. An example of the nucleic acid analysis method according to the embodiment which includes the process J' is illustrated in FIG. 11. Since the process J' is performed after the nucleic acid quantification process B and before the nucleic acid purification process P, it is possible to select the interruption of the nucleic acid analysis before the process P is performed, and it is possible to prevent an incorrect nucleic acid analysis result being obtained. Moreover, it is possible to reduce the amount of reagent required for the process P.

Still further, in each embodiment described above, it is preferable that the biological sample be at least one selected from the group of whole blood, serum, saliva, sputum, oral mucosa, and a tissue slice. In consideration of physical burden of a subject, and a labor at the time of the collection, the biological sample is more preferably whole blood or serum, and is further preferably serum.

If whole blood is used as a biological sample, the nucleic acid that is obtained from blood cell components which are unrelated to the mutation is mainly taken out, and the nucleic acid that is derived from the tissue where the gene mutation occurs has a small amount, and therefore detection is apt to be difficult. Therefore, when the gene mutation is the target, the sample is obtained by directly cutting off the tissue where the mutation is suspected, and thereby it is possible to secure a percentage and an absolute amount of the mutation. However, it is preferable that a minimally invasive technique be used for the sample collection from the tissue since the physical burden of the subjects, and the labor at the time of the collection are significant. Therefore, the use of circulating DNA derived from the tissue and released in the serum which does not include blood cell components is considered to be effective. However, in the technique of the related art, there is a concern that the quantity of nucleic acid collected from serum cannot secure the sensitivity intended in the gene analysis. Accordingly, the nucleic acid analysis method according to the embodiment of the present invention is more suitable for the case where the biological sample is serum.

Moreover, against the irregular result in the presence and absence of the particular nucleic acid sequence or the analysis of the gene polymorphism described above, by using the nucleic acid analysis method according to the embodiment of the present invention, it becomes easy to take a countermeasure at the time of a retest.

[Tenth Embodiment]

In each embodiment described above, the nucleic acid analysis method may include, instead of the process B, a nucleic acid quantification process B' including b'1) a process of injecting the sample containing the same nucleic acid as the nucleic acid which may be analyzed in the analysis well into the quantification well, b'2) a measurement process of measuring ultraviolet absorbance of the sample in the quantification well, and b'3) a process of calculating the amount of the nucleic acid contained in the sample which may be analyzed in the analysis well from the ultraviolet absorbance which is measured in the measurement process.

The calculation of the amount the nucleic acid by ultraviolet absorbance may be performed by a well-known method. The embodiment is a nucleic acid analysis process including the process B' instead of the process B. Since the description of the nucleic acid analysis process including the process B' overlaps with the description of the embodiment of each nucleic acid analysis method described above, the description thereof will be omitted.

EXAMPLES

Next, the present invention will be described in more detail by examples, but the present invention is not limited to the following examples.

1) Selection of Quantification Reagent Concentration

As a quantification reagent, SYBR Green I which is a material specifically associated with double-stranded DNA was selected. SYBR Green I is an asymmetric fluorescent material of the cyanine system, and has a feature of emitting fluorescence at 522 nm as a maximum when irradiated with excitation light of 488 nm at the time of entering (intercalating) between the bases of the double-stranded DNA.

2) Optimization of Quantification Reagent Concentration

Optimum magnification selection of SYBR Green I was performed. A reaction solution of 10μl per one well consisting of $MgCl_2$ of 6.25 mM, NaCl of 15 mM, trehalose of 80 mM, SYBR Green I (written as SG, hereinafter) and standard genome DNA was prepared for the necessary amount. At that time, the reaction solution was prepared so that the magnifications of SG became 1, 2, 3, 4, 5, 6, 7, 8, 9, 10, 15, 20, 30, 40, 50, 60, 70, 80, 90, and 100× (times) in each of the respective quantification wells, and the check of the SG magnification in which fluorescence intensity becomes highest was performed.

Moreover, standard genome DNA (from Coryell Laboratory) was prepared so as to become 0.05, 0.4, and 2.5 ng/μL per one well of the quantification wells with respect to SG of each magnification, and it was confirmed at the same time whether the optimum SG magnification depends on a concentration of the sample. The prepared reaction solution was injected into a 96-well plate separated by each of the genome DNA concentration, and was measured for 20 minutes at 40° C. with a detection wavelength of 520 nm and excitation wavelength of 488 nm by Light Cycler 480 manufactured by Roche Company.

Figure 12:
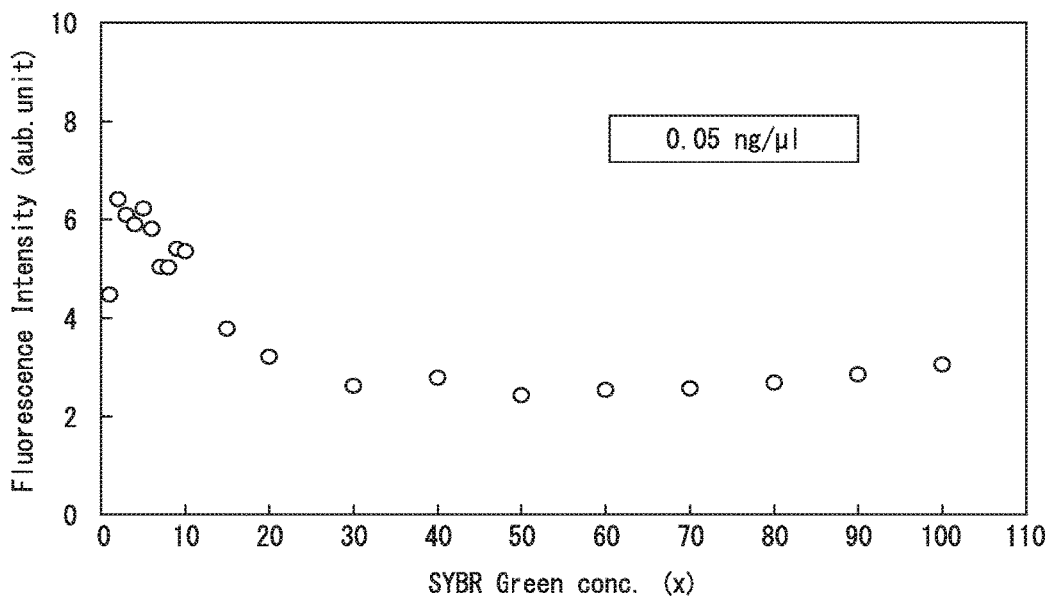
FIG. 12 is a graph illustrating dye concentration optimization with respect to standard DNA (0.05 ng/μL).
Figure 13:
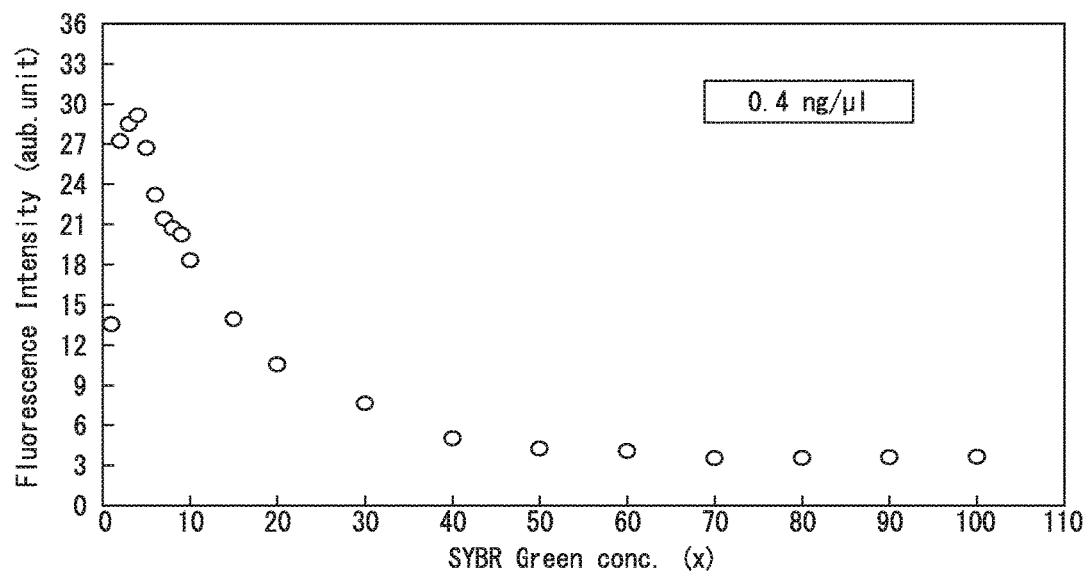
FIG. 13 is a graph illustrating the dye concentration optimization with respect to standard DNA (0.1 ng/μL).
Figure 14:
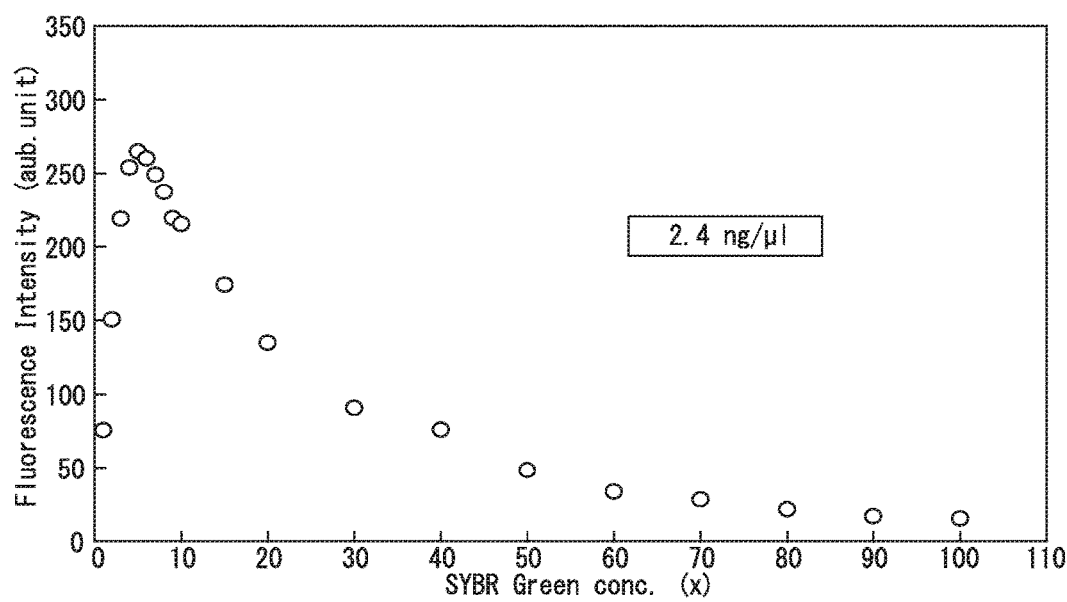
FIG. 14 is a graph illustrating the dye concentration optimization with respect to standard DNA (2.4 ng/μL).

A value of a vertical axis of a graph illustrated in FIG. 12 to FIG. 14 is the fluorescence intensity (unit is arbitrary unit) obtained under the presence of the standard genome DNA of each concentration, and a horizontal axis illustrates the SG magnification. In the test, when the SG magnification was in the vicinity of 2× at the standard genome DNA concentration of 0.05 ng/μL, and 4× was at 0.4 ng/μL, and the SG magnification was 5× at 2.5 ng/μL, the fluorescence intensity became the maximum. It was confirmed that the SG magnification at which the fluorescence intensity becomes the maximum became higher along with the increase of the DNA concentration. From the light-emitting principle illustrated in FIG. 2, it is considered that the fluorescence intensity becomes high since a gap where the dye enters is increased as the concentration of the sample DNA becomes high. Moreover, it was found out that if the SG magnification becomes high to a certain degree in any of the DNA concentrations, the intensity of the fluorescence emission decreased and became lower than the value at the time of 1×. It is considered that SG is supersaturated with respect to the sample DNA, and a concentration quenching by the increase of the fluorochrome concentration occured.

3) Linearity of Fluorescence Intensity with Respect to Sample Concentration

Linearity with respect to the sample composition when SYBR Green I is used, was confirmed. The solution having the composition of $MgCl_2$ of 6.25 mM, NaCl of 15 mM, and the standard DNA which became 0.05, 0.1, 0.4, 0.8, and 1.2 ng/μL per one well, and the genome DNA (confirmed to be 0.95 ng/μL by Pico Green method) which was extracted from whole blood, were respectively prepared. The sample DNA solution of each concentration was injected into a gene analysis device and a gene analysis chip (see Japanese Patent No. 4962658 and Japanese Patent No. 4911264) where SG was dried and fixed so as to be 4× of the final concentration in advance. After the sample injection, the dried and fixed SG and the sample were sufficiently mixed, and the mineral oil was further injected for the purpose of preventing evaporation of the sample solution.

Figure 16:
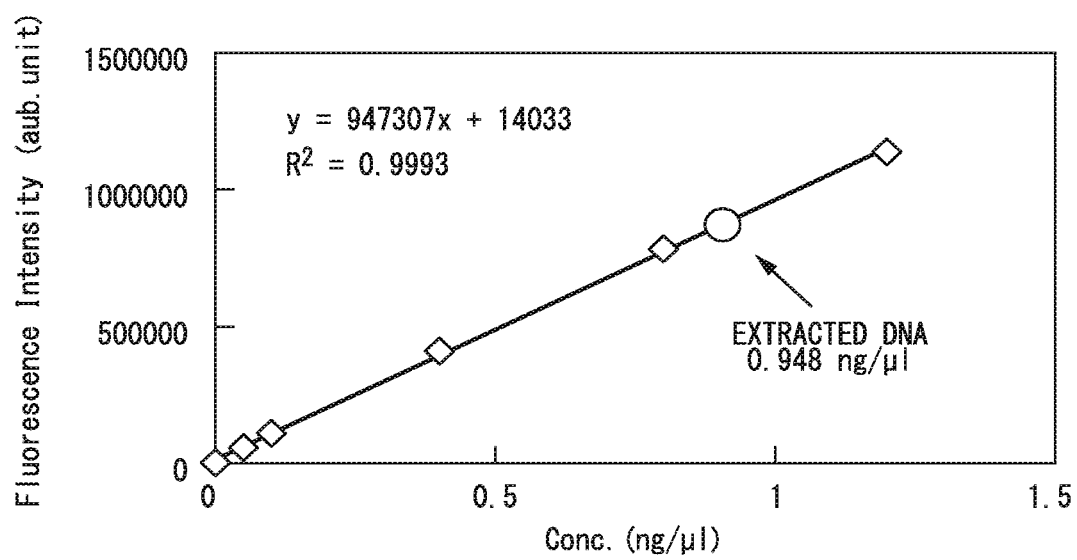
FIG. 16 is a graph illustrating a calibration curve of the DNA concentration dependence of the fluorescence intensity.

For the chip to which the sample DNA was fed, the fluorescence measurements of three times were performed by each sample concentration, at 40° C., with 10 cycles as 1 cycle of 30 seconds, for five minutes in total. A calibration curve was made by averaging the values of the fluorescence intensities which were obtained by the respective sample concentrations on the basis of the result. As a result, $R^2$ exceeded 0.999 as illustrated in FIG. 16, and it was possible to detect the amount of the DNA with high accuracy.

4) Quantification of Amount of DNA Extracted from Whole Blood

Figure 15:
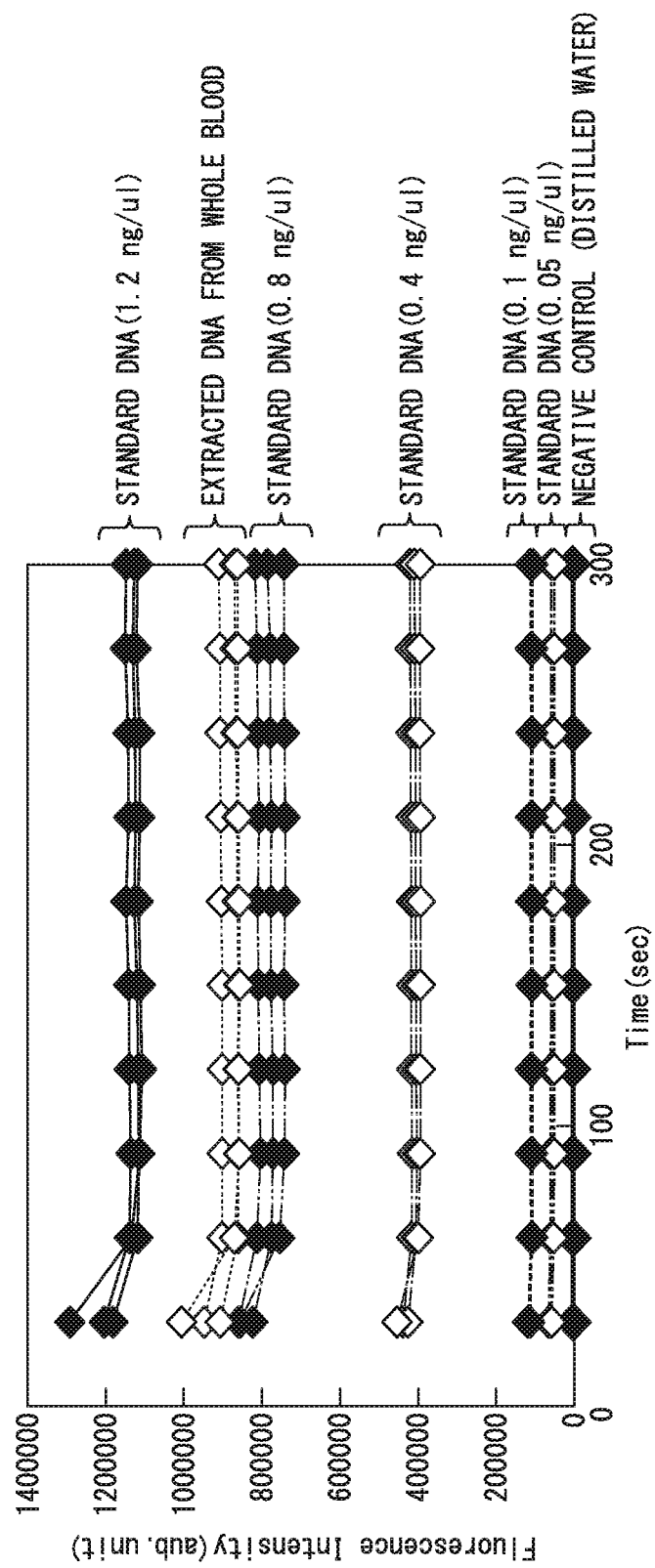
FIG. 15 is a graph illustrating DNA concentration dependence of fluorescence intensity.

As a result of performing an operation which was similar to the confirmation of the above linearity and quantifying the DNA extracted from whole blood, the DNA extracted from whole blood was settled into between the value of the fluorescence intensity in which the standard genome DNA of 0.8 ng/μL and the value of the fluorescence intensity in which the standard genome DNA of 1.2 ng/μL, as illustrated in FIG. 15. As a result of calculating the concentration of the DNA extracted from whole blood by using the calibration curve, it overlapped to 0.95 ng/μL the value of which was obtained by Pico Green method in advance, as illustrated in FIG. 16.

While the embodiments of the present invention are described in detail by the examples with reference to the drawings, the specific configuration is not limited to the embodiments, and includes a design change of the scope without departing from the scope of the present invention.

According to the reaction container, the nucleic acid analysis device, and the nucleic acid analysis method of the present invention, it is possible to enhance the reliability and the accuracy of the analysis result by grasping the amount of the nucleic acid taken out from the biological sample. Therefore, they are suitably used in the fully automatic gene analysis system in which it is difficult to confirm the amount of the nucleic acid obtained from the biological sample. Moreover, they may be widely used in the medical field, the drug development field or the like, and the improvement in the quality of the order-made (personalized) medicine is expected.

What is claimed is:

1. A reaction container, comprising:
a base material;
an injection port arranged on the base material;
an analysis well in which a nucleic acid analysis reagent used for a nucleic acid analysis is contained, the analysis well being arranged on the base material and configured to analyze a sample containing a nucleic acid; and
a quantification well in which a quantification reagent configured to specifically detect the nucleic acid is contained, the quantification well being arranged on the base material and configured to quantify an amount of the nucleic acid contained in the sample before an amplification of the nucleic acid,
a flow path arranged on the base material configured to distribute the nucleic acid contained in the sample into the quantification well and the analysis well,
wherein the nucleic acid contained in the sample is directly distributed into the quantification well and the analysis well respectively by the flow path, and
wherein the quantification well is positioned to be closer to the injection port than the analysis well.

2. The reaction container according to claim 1, wherein the base material is formed from a resin having light-transmitting properties.

3. The reaction container according to claim 1, wherein the injection port is arranged on the base material and configured so that a solution is injectable into the injection port.

4. The reaction container according to claim 1, wherein at least one of the quantification reagent and the nucleic acid analysis reagent is contained in a dry state.

5. The reaction container according to claim 1, wherein at least one of the quantification reagent and the nucleic acid analysis reagent is contained in a dry state and in a state of being mixed with trehalose.

6. A nucleic acid analysis device, comprising:
the reaction container according to claim 1; and
an extraction section to extract the nucleic acid.

7. The nucleic acid analysis device according to claim 6, further comprising:
a purification section to purify the nucleic acid.

8. A nucleic acid analysis method using the reaction container according to claim 1, the method comprising:
a nucleic acid quantification process of
injecting the sample containing the nucleic acid analyzed in the analysis well into the quantification well,
forming an association state in which the nucleic acid contained in the sample and the quantification reagent are associated in the quantification well,
measuring a signal which is emitted in the association state, and
calculating an amount of the nucleic acid analyzed in the analysis well from the measured signal.

9. The nucleic acid analysis method according to claim 8, further comprising:
a nucleic acid extraction process of extracting the nucleic acid from a biological sample performed before the nucleic acid quantification process; and
a nucleic acid analysis process of performing identification of the nucleic acid in the analysis well by injecting the sample containing the nucleic acid into the analysis well performed after the nucleic acid extraction process, wherein
the nucleic acid is obtained in the nucleic acid extraction process.

10. The nucleic acid analysis method according to claim 9, further comprising:
a process of determining validity of an analysis result obtained by the nucleic acid analysis process based on the amount of the nucleic acid calculated by the nucleic acid quantification process performed after the nucleic acid quantification process.

11. The nucleic acid analysis method according to claim 9, further comprising:
a nucleic acid purification process performed after the nucleic acid extraction process and before the nucleic acid quantification process.

12. The nucleic acid analysis method according to claim 9, wherein
the nucleic acid analysis process is performed after the nucleic acid quantification process, and
a nucleic acid purification process performed after the nucleic acid quantification process and before the nucleic acid analysis process is included.

13. The nucleic acid analysis method according to claim 12, further comprising:
a process of determining whether or not a transition to the nucleic acid purification process is performed according to the amount of the nucleic acid calculated by the nucleic acid quantification process, which is performed after the nucleic acid quantification process and before the nucleic acid purification process.

14. The nucleic acid analysis method according to claim 9, wherein
the nucleic acid analysis process is performed after the nucleic acid quantification process, and
a process of determining whether or not a transition to the nucleic acid analysis process is performed according to the amount of the nucleic acid calculated by the nucleic acid quantification process, which is performed after the nucleic acid quantification process and before the nucleic acid analysis process, is further included.

15. The nucleic acid analysis method according to claim 9, wherein
the biological sample is at least one selected from the group of whole blood, serum, saliva, sputum, oral mucosa, and a tissue slice.

16. A reaction container, comprising:
a base material;
an injection port arranged on the base material;
an analysis well in which a nucleic acid analysis reagent used for a nucleic acid analysis is contained, the analysis well being arranged on the base material and configured to analyze a sample containing a nucleic acid; and
a quantification well arranged on the base material and configured to quantify an amount of the nucleic acid contained in the sample before an amplification of the nucleic acid,
a flow path arranged on the base material configured to distribute the nucleic acid contained in the sample into the quantification well and the analysis well,
wherein the nucleic acid contained in the sample is directly distributed into the quantification well and the analysis well respectively by the flow path, and
wherein the quantification well is positioned to be closer to the injection port than the analysis well.

17. The reaction container according to claim 16, wherein the base material is formed from a resin having light-transmitting properties.

18. The reaction container according to claim 16, wherein the injection port arranged on the base material and configured so that a solution is injectable into the injection port.

19. A nucleic acid analysis device, comprising:
the reaction container according to claim 16; and
an extraction section to extract the nucleic acid.

20. The nucleic acid analysis device according to claim 19, further comprising:
a purification section to purify the nucleic acid.

21. A nucleic acid analysis method using the reaction container according to claim 16, the method comprising:
a nucleic acid quantification process of
injecting the sample containing the nucleic acid analyzed in the analysis well into the quantification well,
measuring ultraviolet absorbance of the sample in the quantification well, and
calculating an amount of the nucleic acid analyzed in the analysis well from the measured ultraviolet absorbance.

22. The nucleic acid analysis method according to claim 21, further comprising:
a nucleic acid extraction process of extracting nucleic acid from a biological sample performed before the nucleic acid quantification process; and
a nucleic acid analysis process of performing identification of the nucleic acid in the analysis well by injecting the sample containing the nucleic acid into the analysis well performed after the nucleic acid extraction process, wherein
the nucleic acid is obtained in the nucleic acid extraction process.

23. The nucleic acid analysis method according to claim 22, further comprising:
a process of determining validity of an analysis result obtained by the nucleic acid analysis process based on the amount of the nucleic acid calculated by the nucleic acid quantification process performed after the nucleic acid quantification process.

24. The nucleic acid analysis method according to claim 22, further comprising:
a nucleic acid purification process performed after the nucleic acid extraction process and before the nucleic acid quantification process.

25. The nucleic acid analysis method according to claim 22, wherein
the nucleic acid analysis process is performed after the nucleic acid quantification process, and
a nucleic acid purification process performed after the nucleic acid quantification process and before the nucleic acid analysis process is included.

26. The nucleic acid analysis method according to claim 25, further comprising:
a process of determining whether or not a transition to the nucleic acid purification process is performed according to the amount of the nucleic acid calculated by the nucleic acid quantification process, which is performed after the nucleic acid quantification process and before the nucleic acid purification process.

27. The nucleic acid analysis method according to claim 22, wherein
the nucleic acid analysis process is performed after the nucleic acid quantification process, and
a process of determining whether or not a transition to the nucleic acid analysis process is performed according to the amount of the nucleic acid calculated by the nucleic acid quantification process, which is performed after the nucleic acid quantification process and before the nucleic acid analysis process, is further included.

28. The nucleic acid analysis method according to claim 22, wherein
the biological sample is at least one selected from the group of whole blood, serum, saliva, sputum, oral mucosa, and a tissue slice.

* * * * *